United States Patent
Pham et al.

(10) Patent No.: US 9,737,638 B2
(45) Date of Patent: Aug. 22, 2017

(54) POLYESTER AMIDE COPOLYMERS HAVING FREE CARBOXYLIC ACID PENDANT GROUPS

(75) Inventors: Nam D. Pham, San Jose, CA (US); Michael H. Ngo, San Jose, CA (US); Mikael O. Trollsas, San Jose, CA (US)

(73) Assignee: ABBOTT CARDIOVASCULAR SYSTEMS, INC., Santa Clara, CA (US)

( * ) Notice: Subject to any disclaimer, the term of this patent is extended or adjusted under 35 U.S.C. 154(b) by 1135 days.

(21) Appl. No.: 11/820,833

(22) Filed: Jun. 20, 2007

(65) Prior Publication Data
US 2008/0314289 A1    Dec. 25, 2008

(51) Int. Cl.
A61L 29/08     (2006.01)
A61L 27/34     (2006.01)
A61L 31/10     (2006.01)

(52) U.S. Cl.
CPC ............. *A61L 29/085* (2013.01); *A61L 27/34* (2013.01); *A61L 31/10* (2013.01)

(58) Field of Classification Search
None
See application file for complete search history.

(56) References Cited

U.S. PATENT DOCUMENTS

| | | | |
|---|---|---|---|
| 4,304,767 A | 12/1981 | Heller et al. | |
| 4,733,665 A | 3/1988 | Palmaz | |
| 4,800,882 A | 1/1989 | Gianturco | |
| 4,886,062 A | 12/1989 | Wiktor | |
| 5,272,012 A | 12/1993 | Opolski | |
| 5,581,387 A | 12/1996 | Cahill | |
| 5,702,754 A | 12/1997 | Zhong | |
| 5,861,387 A | 1/1999 | Labrie et al. | |
| 5,869,127 A | 2/1999 | Zhong | |
| 5,997,517 A | 12/1999 | Whitbourne | |
| 6,001,117 A | 12/1999 | Huxel et al. | |
| 6,099,563 A | 8/2000 | Zhong | |
| 6,110,483 A | 8/2000 | Whitbourne et al. | |
| 6,179,817 B1 | 1/2001 | Zhong | |
| 6,197,051 B1 | 3/2001 | Zhong | |
| 6,231,590 B1 | 5/2001 | Slaikeu et al. | |
| 6,274,164 B1 | 8/2001 | Novich | |
| 6,306,176 B1 | 10/2001 | Whitbourne | |
| 6,494,862 B1 | 12/2002 | Ray et al. | |
| 6,503,538 B1 | 1/2003 | Chu et al. | |
| 6,544,223 B1 | 4/2003 | Kokish | |
| 6,544,543 B1 | 4/2003 | Mandrusov et al. | |
| 6,656,216 B1 | 12/2003 | Hossainy et al. | |
| 6,656,506 B1 | 12/2003 | Wu et al. | |
| 6,663,662 B2 | 12/2003 | Pacetti et al. | |
| 6,663,880 B1 | 12/2003 | Roorda et al. | |
| 6,673,154 B1 | 1/2004 | Pacetti et al. | |
| 6,703,040 B2 * | 3/2004 | Katsarava et al. | 424/444 |
| 6,712,845 B2 | 3/2004 | Hossainy | |
| 6,743,462 B1 | 6/2004 | Pacetti | |
| 6,753,071 B1 | 6/2004 | Pacetti | |
| 6,758,859 B1 | 7/2004 | Dang et al. | |
| 6,790,228 B2 | 9/2004 | Hossainy et al. | |
| 6,818,063 B1 | 11/2004 | Kerrigan | |
| 6,824,559 B2 | 11/2004 | Michal | |
| 6,926,919 B1 | 8/2005 | Hossainy et al. | |
| 6,972,054 B2 | 12/2005 | Kerrigan | |
| 7,005,137 B1 | 2/2006 | Hossainy et al. | |
| 7,022,334 B1 | 4/2006 | Ding | |
| 7,056,591 B1 | 6/2006 | Pacetti et al. | |
| 7,060,093 B2 | 6/2006 | Dang et al. | |
| 7,074,276 B1 | 7/2006 | Van Sciver et al. | |
| 7,115,300 B1 | 10/2006 | Hossainy | |
| 7,135,038 B1 | 11/2006 | Limon | |
| 7,166,680 B2 | 1/2007 | DesNoyer et al. | |
| 7,169,178 B1 | 1/2007 | Santos et al. | |
| 7,175,874 B1 | 2/2007 | Pacetti | |
| 7,201,935 B1 | 4/2007 | Claude et al. | |
| 7,202,325 B2 | 4/2007 | Hossainy | |
| 7,217,426 B1 | 5/2007 | Hossainy | |
| 7,220,816 B2 | 5/2007 | Pacetti et al. | |
| 7,232,490 B1 | 6/2007 | Hossainy | |
| 7,232,573 B1 | 6/2007 | Ding | |
| 7,244,443 B2 | 7/2007 | Pacetti | |
| 7,247,313 B2 | 7/2007 | Roorda et al. | |
| 7,255,891 B1 | 8/2007 | Pacetti | |
| 7,261,946 B2 | 8/2007 | Claude | |
| 7,288,609 B1 | 10/2007 | Pacetti | |
| 7,294,329 B1 | 11/2007 | Ding | |
| 7,311,980 B1 | 12/2007 | Hossainy et al. | |
| 7,323,209 B1 | 1/2008 | Esbeck et al. | |
| 7,329,413 B1 | 2/2008 | Pacetti | |
| 7,335,265 B1 | 2/2008 | Hossainy | |
| 7,335,391 B1 | 2/2008 | Pacetti | |
| 7,341,630 B1 | 3/2008 | Pacetti | |
| 7,354,480 B1 | 4/2008 | Kokish et al. | |
| 7,390,497 B2 | 6/2008 | Desnoyer et al. | |
| 7,390,524 B1 | 6/2008 | Chen | |
| 7,396,539 B1 | 7/2008 | Hossainy et al. | |

(Continued)

FOREIGN PATENT DOCUMENTS

WO    WO 2005/000939    1/2005
WO    WO 2005/121250    12/2005

OTHER PUBLICATIONS

Jokhadze, G.; Machaidze, M.; Panosyan, H.; Chu, C. C.; Katsarava, R., Synthesis and characterization of functional elastomeric poly-(ester amide) co-polymers,. Journal of Biomaterials Science—Polymer Edition, Apr. 2007, vol. 18 Issue 4, p. 411-438, 28p, 4 charts, 8 graphs; DOI: 10.1163/156856207780425031; (AN 24713444).*

Trollsas, Mikael et al., Hydrophilic Aliphatic Polyesters: Design, Synthesis and Ring-Opening Polymerization of Functional Cyclic Esters, Macromolecules, 2000, 33, 4619-4627.*

Kobmehl, Gerhard, et al., Alkoxy-substituted liquid-crystallin aromatic copolyesters, Polymer Bulletin 34, 503-508 (1995).*

(Continued)

*Primary Examiner* — Dennis J Parad
*Assistant Examiner* — Lyndsey Beckhardt
(74) *Attorney, Agent, or Firm* — Squire Patton Boggs (US) LLP

(57) ABSTRACT

A poly(ester amide) polymer having free carboxylic acid pendant groups and method of making and using the same are disclosed.

13 Claims, 1 Drawing Sheet

(56) References Cited

U.S. PATENT DOCUMENTS

| | | |
|---|---|---|
| 7,419,504 B2 | 9/2008 | Hossainy |
| 7,431,959 B1 | 10/2008 | Dehnad |
| 7,435,788 B2 | 10/2008 | Pacetti |
| 7,481,835 B1 | 1/2009 | Pacetti et al. |
| 7,494,665 B1 | 2/2009 | Ding et al. |
| 7,504,125 B1 | 3/2009 | Pacetti et al. |
| 7,563,454 B1 | 7/2009 | Pacetti |
| 7,604,818 B2 | 10/2009 | Pacetti |
| 7,628,859 B1 | 12/2009 | Hossainy et al. |
| 7,632,307 B2 | 12/2009 | Pacetti et al. |
| 2001/0007083 A1 | 7/2001 | Roorda |
| 2003/0073961 A1 | 4/2003 | Happ |
| 2003/0082368 A1 | 5/2003 | Reuter et al. |
| 2003/0104028 A1 | 6/2003 | Hossainy et al. |
| 2003/0105518 A1 | 6/2003 | Dutta |
| 2003/0158517 A1 | 8/2003 | Kokish |
| 2004/0047980 A1 | 3/2004 | Pacetti et al. |
| 2004/0052858 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0142015 A1 | 7/2004 | Hossainy et al. |
| 2004/0162609 A1 | 8/2004 | Hossainy et al. |
| 2004/0180132 A1 | 9/2004 | Pacetti |
| 2004/0182312 A1 | 9/2004 | Pacetti et al. |
| 2004/0191405 A1 | 9/2004 | Kerrigan |
| 2004/0253203 A1 | 12/2004 | Hossainy et al. |
| 2005/0021127 A1 | 1/2005 | Kawula |
| 2005/0025799 A1 | 2/2005 | Hossainy et al. |
| 2005/0074544 A1 | 4/2005 | Pacetti et al. |
| 2005/0106204 A1 | 5/2005 | Hossainy et al. |
| 2005/0112170 A1 | 5/2005 | Hossainy et al. |
| 2005/0112171 A1 | 5/2005 | Tang et al. |
| 2005/0118344 A1 | 6/2005 | Pacetti |
| 2005/0147647 A1 | 7/2005 | Glauser |
| 2005/0169957 A1 | 8/2005 | Hossainy |
| 2005/0175666 A1 | 8/2005 | Ding |
| 2005/0208091 A1 | 9/2005 | Pacetti |
| 2005/0214339 A1 | 9/2005 | Tang et al. |
| 2005/0226991 A1 | 10/2005 | Hossainy et al. |
| 2005/0244363 A1 | 11/2005 | Hossainy et al. |
| 2005/0245637 A1 | 11/2005 | Tang et al. |
| 2005/0265960 A1 | 12/2005 | Pacetti et al. |
| 2005/0271700 A1 | 12/2005 | Desnoyer et al. |
| 2005/0287184 A1 | 12/2005 | Hossainy et al. |
| 2006/0002968 A1 | 1/2006 | Stewart et al. |
| 2006/0034888 A1 | 2/2006 | Pacetti et al. |
| 2006/0043650 A1 | 3/2006 | Hossainy et al. |
| 2006/0062824 A1 | 3/2006 | Pacetti et al. |
| 2006/0074191 A1* | 4/2006 | DesNoyer et al. ........... 525/178 |
| 2006/0089485 A1 | 4/2006 | Desnoyer et al. |
| 2006/0095122 A1 | 5/2006 | Pacetti |
| 2006/0115449 A1 | 6/2006 | Pacetti |
| 2006/0115513 A1 | 6/2006 | Hossainy |
| 2006/0147412 A1 | 7/2006 | Hossainy et al. |
| 2007/0032853 A1 | 2/2007 | Hossainy et al. |

OTHER PUBLICATIONS

Ki, H. C., et al, Synthesis, characterization and biodegradability of the biodegradable aliphatic-aromatic random copolyesters, Polymer, 42 (2001) 1849-1861.*

Sahoo, Bishwabhusan, et al., Biomacromolecules, 7 (2006), pp. 1042-1048.*

Guan, Hui-Li, et al, Journal of Polymer Science: Part A: Polymer Chemistry, vol. 43, (2005), pp. 1144-1149.*

U.S. Appl. No. 10/815,421, filed Mar. 31, 2004, Hossainy.
U.S. Appl. No. 10/820,316, filed Aug. 7, 2004, Hossainy et al.
U.S. Appl. No. 10/835,656, filed Apr. 30, 2004, Tang et al.
U.S. Appl. No. 10/835,912, filed Apr. 30, 2004, Hossainy et al.
U.S. Appl. No. 10/851,411, filed May 20, 2004, Chen.
U.S. Appl. No. 10/855,294, filed May 26, 2004, Pacetti et al.
U.S. Appl. No. 10/881,540, filed Jun. 29, 2004, Hossainy et al.
U.S. Appl. No. 10/882,506, filed Jun. 30, 2004, Stewart et al.
U.S. Appl. No. 10/883,242, filed Jun. 30, 2004, Roorda et al.
U.S. Appl. No. 10/902,982, filed Jul. 30, 2004, Pacetti et al.
U.S. Appl. No. 10/909,795, filed Jul. 30, 2004, Ding et al.
U.S. Appl. No. 10/910,453, filed Aug. 2, 2004, Hossainy et al.
U.S. Appl. No. 10/913,607, filed Aug. 5, 2004, Pacetti et al.
U.S. Appl. No. 10/928,587, filed Aug. 26, 2004, Hossainy et al.
U.S. Appl. No. 10/931,927, filed Aug. 31, 2004, Pacetti.
U.S. Appl. No. 10/932,364, filed Aug. 31, 2004, Foreman et al.
U.S. Appl. No. 10/948,036, filed Sep. 22, 2004, Pacetti et al.
U.S. Appl. No. 10/975,247, filed Oct. 27, 2004, Desnoyer et al.
U.S. Appl. No. 10/976,550, filed Oct. 29, 2004, Pacetti et al.
U.S. Appl. No. 10/976,551, filed Oct. 29, 2004, DesNoyer et al.
U.S. Appl. No. 10/999,391, filed Nov. 29, 2004, Hossainy.
U.S. Appl. No. 10/978,031, filed Oct. 29, 2004, Pacetti.
U.S. Appl. No. 11/000,572, filed Nov. 30, 2004, Pacetti.
U.S. Appl. No. 11/015,313, filed Dec. 16, 2004, Pacetti et al.
U.S. Appl. No. 11/021,775, filed Dec. 22, 2004, Pacetti.
U.S. Appl. No. 11/023,837, filed Dec. 27, 2004, Hossainy.
U.S. Appl. No. 11/027,822, filed Dec. 29, 2004, Ding.
U.S. Appl. No. 11/027,955, filed Dec. 30, 2004, Hossainy et al.
U.S. Appl. No. 11/035,816, filed Jan. 14, 2005, Hossainy.

Chandrasekar et al., *Coronary Artery Endothelial Protection After Local Delivery of 17β-Estradiol During Balloon Angioplasty in a Porcine Model: A Potential New Pharmacologic Approach to Improve Endothelial Function*, J. of Am. College of Cardiology, vol. 38, No. 5, (2001) pp. 1570-1.576.

Detrembleur et al., *Ring-Opening Polymerization of γ-Bromo-ε-caprolactone: A Novel Route to Functionalized Aliphatic Polyesters*, Macromolecules 33, (2000) pp. 14-18.

De Lezo et al., *Intracoronary Ultrasound Assessment of Directional Coronary Atherectomy: Immediate and Follow-Up Findings*, JACC vol. 21, No. 2, (1993) pp. 298-307.

Gohy et al., *Synthesis and characterization of non-covalent liquid crystalline diblock copolymers*, Macromol. Chem. Phys. 201, (2000) pp. 31-41.

Moreno et al., *Macrophage Infiltration Predicts Restenosis After Coronary Intervention in Patients with Unstable Angina*, Circulation, vol. 94, No. 12, (1996) pp. 3098-3102.

Oikawa et al., *Mechanisms of Acute Gain and Late Lumen Loss After Atherectomy in Different Preintervention Arterial Remodeling Patterns*, The Am. J. of Cardilogy, vol. 89, (2002) pp. 505-510.

Parrish et al., *PED-and Peptide-Grafted Aliphatic Polyesters by Click Chemistry*, J. Am. Chem. Soc. vol. 127, No. 20 (2005) pp. 7404-7410.

Scully et al., *Effect of a heparan sulphate with high affinity for antithrombin III upon inactivation of thrombin and coagulaton Factor Xa*, Biochem J. 262, (1989) pp. 651-658.

Virmani et al., *Lessons From Sudden Coronary Death a Comprehensive Morphological Classification Scheme for Atherosclerotic Lesions*, Arterioscler Thromb Vasc Biol. (2000) pp. 1262-1275.

International Search Report mailed Oct. 5, 2009 for PCT/US2008/066764, mailed Oct. 5, 2009, 17 pgs.

Jokhadze et al., "Synthesis and characterization of functional elastomeric poly(ester amide) co-polymers", J. Biomater. Sci. Polymer Edn. Vo9l. 18, No. 4, pp. 411-438 (2007).

U.S. Appl. No. 09/406,473, filed Sep. 27, 1999, Pacetti.
U.S. Appl. No. 10/177,942, filed Jun. 21, 2002, Michal et al.
U.S. Appl. No. 10/316,739, filed Dec. 10, 2002, Zhang et al.
U.S. Appl. No. 10/375,496, filed Feb. 26, 2003, Esbeck.
U.S. Appl. No. 10/376,348, filed Feb. 26, 2003, Ding et al.
U.S. Appl. No. 10/606,711, filed Jun. 26, 2003, Pacetti.
U.S. Appl. No. 10/606,712, filed Jun. 26, 2003, Pacetti.
U.S. Appl. No. 10/705,546, filed Nov. 10, 2003, Kwok et al.
U.S. Appl. No. 10/714,111, filed Nov. 14, 2003, Claude.
U.S. Appl. No. 10/816,072, filed Mar. 31, 2004, Dugan et al.
U.S. Appl. No. 10/835,229, filed Apr. 28, 2004, Prabhu et al.
U.S. Appl. No. 10/853,924, filed May 25, 2004, Pathak.
U.S. Appl. No. 10/877,419, filed Jun. 25, 2004, Pacetti.

* cited by examiner

US 9,737,638 B2

POLYESTER AMIDE COPOLYMERS HAVING FREE CARBOXYLIC ACID PENDANT GROUPS

FIELD OF THE INVENTION

This invention generally relates to ester amide copolymers, which is a family of biomaterials that can be used in biomedical applications such as coating a stent.

DESCRIPTION OF THE BACKGROUND

Blood vessel occlusions are commonly treated by mechanically enhancing blood flow in the affected vessels, such as by employing a stent. Stents are used not only for mechanical intervention but also as vehicles for providing biological therapy. To effect a controlled delivery of an active agent in stent medication, the stent can be coated with a biocompatible polymeric coating. The biocompatible polymeric coating can function either as a permeable layer or a carrier to allow a controlled delivery of the agent.

Although stents work well mechanically, the chronic issues of restenosis and, to a lesser extent, stent thrombosis remain. Pharmacological therapy in the form of a drug delivery stent appears to be a feasible means to tackle these issues. Polymeric coatings placed onto the stent serve to act both as the drug reservoir and to control the release of the drug. One of the commercially available polymer-coated products is a stent manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition, which includes a bioactive agent, a collagenous material, or a collagenous coating optionally containing or coated with other bioactive agents.

The nature of the coating polymers plays an important role in defining the surface properties of a coating. For example, coating integrity depends largely on the nature of the polymer forming the coating. For example, a very low $T_g$, amorphous coating material can have unacceptable rheological behavior upon mechanical perturbation such as crimping, balloon expansion, etc. On the other hand, a high $T_g$ or highly crystalline coating material can become brittle in the high strain areas of the stent pattern.

Therefore, there is a need for polymeric materials that can be tailored to meet need of a coating on a medical device.

The polymer and methods of making the polymer disclosed herein address the above-described problems.

SUMMARY OF THE INVENTION

Provided herein is a polyester amide (PEA) comprising free carboxylic acid pendant groups. The PEA polymer can form compositions that are biomaterials that can be used for forming fiber, film, coating, particle, and/or gel in many biomedical applications. In addition, a polymer comprising these pendant groups can have short hydrolysis half-life time, thus allowing the polymer to have tunable degradation rate. In addition, large segments or oligomers originating from the polymer backbone can become water soluble as the polymer degrades, which will promote mass transport away from the implanted site and ideally prevent any negative tissue response to the polymer. The polymer can be used for drug delivery, allowing control of drug release by controlled erosion of the polymer.

The number of the pendant groups in the PEA polymer relates to the acidity of the polymer and therefore directly relates to the rate of degradation and the solubility of the degradation products of the PEA polymer. In some embodiments, the PEA polymer can have an acid content of about 25% or above. As used herein, the acid content refers to the molar ratio of the monomers with free carboxylic acid pendant groups to the sum total of the corresponding other monomers in the backbone of the PEA polymer. In some embodiments, the PEA polymer can have an acid content of about 20% or above, about 15% or above, about 15% or above, about 10% or above, about 5% or above, about 1% or above, about 0.5% or above.

In some embodiments, the PEA polymer described herein can have a degradation rate of 50 wt % within about 24 months, within about 12 months, within about 6 months, within about 3 months, within about 2 months, or within about 1 month upon exposure to a physiological fluid (e.g., blood) or a physiological environment (e.g., tissue of a mammal such as a human being).

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these. In some embodiments, the hydrophilic bioactive agent can be a peptide (e.g., RGD, cRGD or mimetics thereof) or a drug carrying a charge.

A medical device having a coating that includes a PEA polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

DETAILED DESCRIPTION

Figure 1:
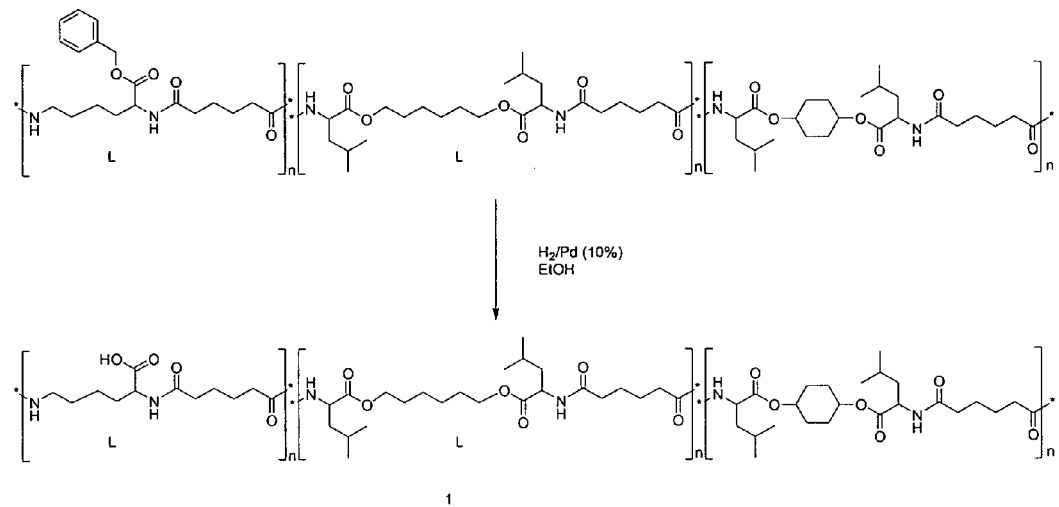
FIGS. 1 and 2 show two examples of polyester amide (PEA) polymer having free carboxylic acid pendant groups and a deprotection step leading to the PEA polymers.

Provided herein is a PEA polymer comprising free carboxylic acid pendant groups. The PEA polymer can form compositions that are biomaterials that can be used for forming fiber, film, coating, particle, and/or gel in many biomedical applications. In addition, a polymer comprising these pendant groups can have short hydrolysis half-life time, thus allowing the polymer to have tunable degradation rate. In addition, large segments or oligomers originating from the polymer backbone can become water soluble as the polymer degrades, which will promote mass transport away from the implanted site and ideally prevent any negative tissue response to the polymer. The polymer can be used for drug delivery, allowing control of drug release by controlled erosion of the polymer.

The number of the pendant groups in the PEA polymer relates to the acidity of the polymer and therefore directly relates to the rate of degradation and the solubility of the degradation products of the PEA polymer. In some embodiments, the PEA polymer can have an acid content of about 25% or above. As used herein, the acid content refers to the molar ratio of the monomers with free carboxylic acid pendant groups to the sum total of the corresponding other monomers in the backbone of the PEA polymer. In some embodiments, the PEA polymer can have an acid content of about 20% or above, about 15% or above, about 15% or above, about 10% or above, about 5% or above, about 1% or above, about 0.5% or above.

In some embodiments, the PEA polymer described herein can have a degradation rate of 50 wt % within about 24 months, within about 12 months, within about 6 months, within about 3 months, within about 2 months, or within about 1 month upon exposure to a physiological fluid (e.g., blood) or a physiological environment (e.g., tissue of a mammal such as a human being).

In some embodiments, the polymer described herein can be used to form a coating on an implantable device, which can optionally include a bioactive agent. The bioactive agent can be any diagnostic agent, therapeutic agent, or preventive agent. Some examples of such bioactive agents include, but are not limited to, paclitaxel, docetaxel, estradiol, 17-beta-estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, dexamethasone acetate, rapamycin, rapamycin derivatives, 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin, or prodrugs, co-drugs, or combinations of these. In some embodiments, the hydrophilic bioactive agent can be a peptide (e.g., RGD, cRGD or mimetics thereof) or a drug carrying a charge.

A medical device having a coating that includes a PEA polymer described herein can be used to treat, prevent, or ameliorate a medical condition such as atherosclerosis, thrombosis, restenosis, hemorrhage, vascular dissection or perforation, vascular aneurysm, vulnerable plaque, chronic total occlusion, claudication, anastomotic proliferation (for vein and artificial grafts), bile duct obstruction, urethra obstruction, tumor obstruction, and combinations thereof.

Polyester Amide Polymers

Polyester amide polymers are polymers that include at least one ester grouping and at least one amide units in the backbone of the polymer. Generally, a PEA polymer can be synthesized using starting materials that form the ester and amide units in the polymer backbone.

In some embodiments, PEA units can be synthesized according to the synthetic techniques as described below in the application. Some exemplary PEA polymers can be products of reaction between at least one reagent of group A, at least one reagent of group B and reagent $C_1$ of group C. The precursor-reagents of groups A, B, and C that can be used are characterized as follows.

As used herein, the group A, group B and group C reagents can sometimes overlap. Some examples of the group A reagents belongs is also provided in Table 1.

TABLE 1

| | | Group A Reagents | |
|---|---|---|---|
| No. | Code | Reagent General Formula | Reagent Definition |
| 1 | $A_1$ | $H_2N-CH(R_1)-C(=O)-O-X-O-C(=O)-CH(R_1)-NH_2$ | Diol-diamine |
| 2 | $A_2$ | $HO-R_2-C(=O)-NH-Y-NH-C(=O)-R_2-OH$ | Amidediol |
| 3 | $A_3$ | HO—X—OH | Diol |
| 4 | $A_4$ | $H_2N-Y-NH_2$ | Diamine |

In the general formulae of compounds $A_1$, $A_2$, $A_3$, and $A_4$ presented in Table 1, the substituents $R_1$, $R_2$, X, and Y can be as follows:

$R_1$—(a) hydrogen;
  (b) methyl (—H$_3$);
  (c) iso-propyl (—-i-C$_3$H$_7$);
  (d) sec-butyl (-sec-C$_4$H$_9$);
  (e) iso-butyl (-i-C$_4$H$_9$); or
  (f) benzyl (—CH$_2$C$_6$H$_5$);

$R_2$—(a) methylene (—CH$_2$—);
  (b) ethylene (—CH$_2$CH$_2$—);
  (c) methylmethylene [—CH(CH$_3$)—];
  (d) straight chained or branched propylene, such as:
    (d1) n-propylene (—CH$_2$CH$_2$CH$_2$—);
    (d2) iso-propylene [—CH$_2$CH(CH$_3$)—]; or
    (d3) ethylmethylene [—CH(CH$_2$CH$_3$)—];
  (e) straight chained or branched butylene, such as:
    (e1) n-butylene (—CH$_2$CH$_2$CH$_2$CH$_2$—),
    (e2) iso-butylene [—CH$_2$CH(CH$_3$)CH$_2$—], or
    (e3) sec-butylene [—CH(CH$_2$CH$_3$)CH$_2$—];
  (f) straight chained or branched pentylene, such as:
    (f1) n-pentylene (—CH$_2$CH$_2$CH$_2$CH$_2$CH$_2$—),
    (f2) iso-pentylene [—C(CH$_3$)$_2$CH$_2$CH$_2$—],
    (f3) neopentylene {—CH[C(CH$_3$)$_3$]—},
    (f4) 2-methyl-1-butylene [—C(CH$_3$)(CH$_2$CH$_3$)CH$_2$—],
    (f5) sec-iso-pentylene [—C(CH$_3$)$_2$CH(CH$_3$)—], or
    (f6) methylpropylmethylene [—C(CH$_3$)(CH$_2$CH$_2$CH$_3$)—]; or
  (g) groups that are present in some amino acids, such as:

(g1) methyleneamide (present in asparagine) [—$CH_2$(CONH$_2$)—];
(g2) ethyleneamide (present in glutamine) [—$CH_2CH_2$(CONH$_2$)—];
(g3) methylmercaptomethylmethylene (present in methionine) [—$CH_2(CH_2SCH_3)$—]; or
(g4) n-propyleneamino group (—$CH_2CH_2CH_2NH$—) which can be derived from 2-pyrrolidine group present (present in proline);
(h) aromatics;
(i) estradiol;
(j) bis-MPA (2,2,-dimethylolpropionic acid) derivatives and similar compounds with protected free acids.

X—straight chained. cyclic or branched aliphatic alkylene group $C_nH_{2n}$, wherein n is an integer between 2 and 16, e.g., methylene, ethylene, propylene, butylene, amylene (pentylene), hexylene, heptylene, octylene, nonylene, decylene, undecylene, or dodecylene group; and Y—straight chained or branched aliphatic alkylene group $C_2H_4$ (ethylene), $C_3H_6$ (propylene), $C_4H_8$ (butylene), or $C_5H_{10}$ (pentylene also known as amylene).

ture, for example, about 130° C., and can be catalyzed by a strong acid or base, e.g., p-toluenesulfonic acid.

In some embodiments, the diol that can be used to make the reagent $A_1$ has the formula HO—X—OH, where X is as defined above. In some embodiments, the diol can be derived from bis-MPA (2,2,-dimethylol propionic acid), for example, bis-MPA protected with a protective group in the carboxylic grouping.

Representative examples of diols that can be used include ethylene glycol, diethylene glycol, triethylene glycol, tetraethylene glycol, pentaethylene glycol, 1,3-cyclohexanediol, 1,3-propanediol, 1,4-butanediol, 1,4-cyclohexanediol, cyclohexane-1,4-dimethanol, 1,5-pentanediol, 1,6-hexanediol, 1,7-heptanediol, 1,8-octanediol, 1,9-nonanediol, 1,10-decanediol, 1,11-undecanediol, and 1,12-dodecanediol. The amino acid that can be used to make the reagent $A_1$ has the formula $H_2N$—$CHR_1$—COOH, where $R_1$ is as defined above. Some amino acids that can be used are summarized in Table 2.

TABLE 2

Amino Acids That Can Be Used for Making the Reagent $A_1$

| No. | $R_1$ | Amino Acid ($H_2N$—CH($R_1$)—COOH) Formula | Name |
|---|---|---|---|
| 1 | —H | $H_2N$—$CH_2$—COOH | Glycine |
| 2 | —$CH_3$ | $H_2N$—CH(—$CH_3$)—COOH | Alanine |
| 3 | -i-$C_3H_7$ | $H_3C$—CH—$CH_3$ / $H_2N$—CH—COOH | Valine |
| 4 | -sec-$C_4H_9$ | $H_3C$—$CH_2$—CH—$CH_3$ / $H_2N$—CH—COOH | Isoleucine |
| 5 | -i-$C_4H_9$ | $CH_3$ / $H_3C$—CH—$CH_2$ / $H_2N$—CH—COOH | Leucine |
| 6 | $C_6H_5CH_2$— | Ph—$CH_2$ / $H_2N$—CH—COOH | phenyl alanine |
| 7 | —$(CH_2)_2$—S—$CH_3$ | $H_2C$—$CH_2$—S—$CH_3$ / $H_2N$—CH—COOH | methionine (α-amino-γ-methylmercaptobutyric acid) |
| 8 | —$CH_2$—C(O)—$NH_2$ | $H_2C$—C(O)—$NH_2$ / $H_2N$—CH—COOH | asparagine (α-amino-succinamic acid) |
| 9 | —$(CH_2)_2$—C(O)—$NH_2$ | $H_2C$—$CH_2$—C(O)—$NH_2$ / $H_2N$—CH—COOH | glutamine (2-amino-glutaramic acid) |

The reagent $A_1$ is a diol-diamine that can be synthesized by condensation of two molar equivalents of an amino acid and one molar equivalent of a diol. The synthesis can be carried under the conditions favoring esterification of the amino acid via the amino acid's carboxyl group. The reaction can be conducted under dehydrating conditions which include anhydrous environment and an elevated tempera- In addition to amino acids listed in Table 2, alternatively other amino acids can be used. One example of such alternative amino acids is proline (2-pyrrolidine carboxylic acid). Other alternative amino acids that can be used include some amino acids having free hydroxyl groups or second carboxyl groups if the free hydroxyl groups or the second carboxyl groups are protected first. The protection is needed so as to avoid interference when reagent $A_1$ is subsequently reacted with reagents of groups B and C, as discussed above. Examples of the amino acids that can be used after the free hydroxyl or second carboxyl groups are protected include tyrosine, serine, or glutamic acid.

The reagent $A_2$ is an amidediol that can be synthesized by condensation of two molar equivalents of a hydroxy acid and one molar equivalent of a diamine. The synthesis can be carried under the conditions favoring formation of an amide bond. The reaction can be conducted under dehydrating conditions which include anhydrous environment, and can be catalyzed by a strong base. Simple heating of the neat starting materials with the simultaneous removal of generated water by distillation can also be used.

The diamine that can be used to make the reagent $A_2$ has the formula $H_2N-Y-NH_2$, where Y is as defined above. Accordingly, examples of diamines that can be used include 1,4-butanediamine (putrescine) ($Y=CH_2CH_2CH_2CH_2$). Alternatively, other diamines, such as 1,2-ethanediamine ($Y=CH_2CH_2$), 1,5-pentanediamine (cadavarene) ($Y=CH_2CH_2CH_2CH_2CH_2$), or 1,4 cyclohexanediamine can be used. The hydroxy acid that can be used to make the reagent $A_2$ has the formula $HO-R_2-COOH$, where $R_2$ is as defined above. Some hydroxy acids that can be used are summarized in Table 3.

The reagent $A_3$ is a common simple diol having the formula $HO-X-OH$, where X is as defined above; and the reagent $A_4$ is a common simple diamine having the formula $H_2N-Y-NH_2$, where Y is as defined above, or alternatively made from lysine where the acid group is protected by esterification with benzyl alcohol or alternatively any other suitable protecting group (for details see Peter G. M. Wuts, Theodora W. Greene, Greene's Protective Groups in Organic Synthesis, $4^{th}$ Edition, Wiley, 2006).

B. Group B Reagents

In some embodiments, the group B reagents that can be used for synthesizing the biologically absorbable copolymers according to embodiments of the present invention are summarized in Table 4. Exemplary definitions used to describe a chemical family to which each of the group B reagents belongs is also provided in Table 4. Note, as indicated above, the group B and group A reagents can sometimes overlap.

TABLE 3

Hydroxy Acids That Can Be Used for Making the Reagent $A_2$

| No. | $R_2$ | Hydroxy Acid ($HO-R_2-COOH$) Formula | Name |
|---|---|---|---|
| 1 | $-CH_2-$ | $HO-CH_2-COOH$ | glycolic (hydroxyacetic) acid |
| 2 | $-CH_2-CH_2-$ | $HO-CH_2-CH_2-COOH$ | β-hydroxypropionic acid |
| 3 | $-\underset{\underset{CH_3}{\|}}{CH}-$ | $HO-\underset{\underset{CH_3}{\|}}{CH}-COOH$ | lactic (α-hydroxypropionic acid) |
| 4 | $-\underset{\underset{CH_3}{\|}}{CH}-CH_2-$ | $HO-\underset{\underset{CH_3}{\|}}{CH}-CH_2-COOH$ | β-hydroxybutyric acid |
| 5 | $-\underset{\underset{CH_2-CH_2-CH_3}{\|}}{CH}-$ | $CH_3-CH_2-CH_2-\underset{\underset{HO}{\|}}{CH}-COOH$ | α-hydroxyvaleric acid |
| 6 | $-\underset{\underset{CH_2-CH_3}{\|}}{CH}-CH_2-$ | $CH_3-CH_2-\underset{\underset{HO}{\|}}{CH}-CH_2-COOH$ | β-hydroxyvaleric acid |
| 7 | $-(CH_2)_5-$ | $HO-(CH_2)_5-COOH$ | ε-hydroxycaproic acid |
| 8 | $-\underset{\underset{CH_2-(CH_2)_2-CH_3}{\|}}{CH}-$ | $CH_3-\underset{\underset{OH}{\|}}{CH}-(CH_2)_3-COOH$ | α-hydroxycaproic acid |
| 8 | $-\underset{\underset{CH_2-CH_2-CH_3}{\|}}{CH}-CH_2-$ | $CH_3-(CH_2)_2-\underset{\underset{OH}{\|}}{CH}-CH_2-COOH$ | β-hydroxycaproic acid |
| 9 | $-\underset{\underset{CH_2-CH_3}{\|}}{CH}-(CH_2)_2-$ | $CH_3-CH_2-\underset{\underset{OH}{\|}}{CH}-(CH_2)_2-COOH$ | δ-hydroxycaproic acid |

TABLE 4

Group B Reagents

| No. | Code | Reagent General Formula | Exemplary Reagent Definition ($R_4$ = PEG) |
|---|---|---|---|
| 1 | $B_1$ | $H_2N-\overset{R_1}{\underset{|}{CH}}-\overset{O}{\underset{\|}{C}}-O-R_4-O-\overset{O}{\underset{\|}{C}}-\overset{R_1}{\underset{|}{CH}}-NH_2$ | PEG-diester-diamine |
| 2 | $B_2$ | $HO-R_2-\overset{O}{\underset{\|}{C}}-NH-R_4-NH-\overset{O}{\underset{\|}{C}}-R_2-OH$ | PEG-amidediol |
| 3 | $B_3$ | $HO-R_4-OH$ | PEG-diol |
| 4 | $B_4$ | $H_2N-R_4-NH_2$ | PEG-diamine |

In general formulae of compounds $B_1$, $B_2$, $B_3$, and $B_4$ presented in Table 4, the substituents $R_1$ and $R_2$ are as defined above. One example of the $R_4$ moiety that can be used is a moiety derived from poly(ethylene glycol) (PEG). Alternatively, other biologically beneficial moieties can be used as $R_4$, for example, moieties derived from poly(propylene glycol) (PPG), random or block copolymers of PEG and PPG, or hyaluronic acid.

The reagent $B_1$ can be a PEG-diester-diamine adduct (i.e., when $R_4$=PEG) that can be synthesized by condensation of two molar equivalents of an amino acid and one molar equivalent of PEG. The synthesis can be carried under the conditions favoring esterification of the amino acid via the carboxyl group. The reaction can be conducted under dehydrating conditions which include anhydrous environment and an elevated temperature, for example, about 130° C., and can be catalyzed by a strong acid or base, e.g., p-toluenesulfonic acid. To make the reagent $B_1$, PEG having molecular weight between about 100 and about 4,000 Daltons, for example, about 300 Daltons, can be used. Any amino acid listed in Table 2 can be used. Alternatively, other amino acids can be used, for example, tyrosine, serine, or glutamic acid, if free hydroxyl groups of tyrosine and serine or the second carboxyl group of glutamic acid are protected so as not to interfere when reagent $B_1$ is subsequently reacted with reagents of groups A and C, as discussed above.

In some embodiments, the reagent $B_2$ can be a PEG-amidediol that can be synthesized by condensation of two molar equivalents of a hydroxy acid and one molar equivalent of a PEG-diamine. The synthesis can be carried out under the conditions favoring formation of an amide bond.

C. Group C Reagents

In some embodiments, the group C reagents that can be used for synthesizing the biologically absorbable copolymers according to embodiments of the present invention are summarized in Table 5. The definition used to describe a chemical family to which each of the group C reagents belongs is also provided in Table 5.

TABLE 5

Group C Reagents

| No. | Code | Reagent General Formula | Reagent Definition |
|---|---|---|---|
| 1 | $C_1$ | $HO-\overset{O}{\underset{\|}{C}}-R_3-\overset{O}{\underset{\|}{C}}-OH$ | Dicarboxylic acid |
| 2 | $C_2$ | $HO-\overset{O}{\underset{\|}{C}}-PEG-\overset{O}{\underset{\|}{C}}-OH$ | PEG-dicarboxylic acid |

In general formula of compound $C_1$ presented in Table 5, the substituent $R_3$ is simply a covalent bond, or a straight chained, cyclic or branched aliphatic alkylene group $C_nH_{2n}$, wherein n is an integer having a value between 0 and 12, e.g. a single bond (n=0), methylene, ethylene, propylene, butylene, amylene (pentylene), hexylene, cyclohexylene, heptylene, octylene, nonylene, decylene, undecylene, or dodecylene group, or an aromatic group, e.g., phenyl or paraphenylene. Alternatively, the aliphatic chains may have pending groups such as alcohols, that may or may not be protected. Some examples of dicarboxylic acids that can be used as the reagent C, are summarized in Table 6, which shows the formula or name or both of the exemplary $C_1$ reagents.

TABLE 6

Dicarboxylic Acids That Can Be Used As the Reagent $C_1$

Dicarboxylic Acid (HOOC—$R_3$—COOH)

| No. | $R_3$ | Formula | Name |
|---|---|---|---|
| 1 | —$(CH_2)_2$— | HOOC—$(CH_2)_2$—COOH | succinic (butanedioic) acid |
| 2 | —$CH_2CCH_3ORCH_2$— | HOOC—$CH_2CCH_3ORCH_2$—COOH | |
| 3 | —$(CH_2)_4$— | HOOC—$(CH_2)_4$—COOH | adipic (hexanedioic) acid |
| 4 | —$(CH_2)_8$— | HOOC—$(CH_2)_8$—COOH | sebacic (decanedioic) acid |
| 5 | (p)-$C_6H_4$— | HOOC-(p)$C_6H_4$—COOH | terephthalic (1,4-benzene dicarboxylic) acid |
| 6 | —$CH(CH_2)_4CH$— | HOOC—$CH(CH_2)_4CH$—COOH | cyclohexane di carboxylic acid |

In addition to the dicarboxylic acids listed in Table 6, examples of other dicarboxylic acids that can be also used include oxalic acid, malonic acid, glutaric acid, pimelic acid, suberic acid, or azelaic acid. As mentioned above, to synthesize the PEAs, at least one reagent of group A can be reacted with at least one reagent of group B and reagent $C_1$.

Some examples of the synthesis of particular polymers are provided below in the "Examples" section of the present application.

As a result of the synthesis, biologically absorbable PEAs having a general formula (A) can be obtained:

$$-[M-P]_m-[M-Q]_n- \quad (A)$$

wherein:

M is a moiety represented by the structure of

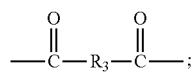

P is a moiety including:

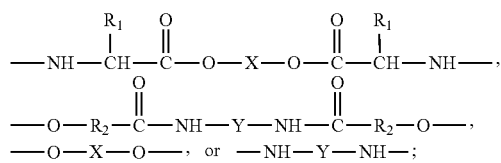

Q is a moiety selected from:

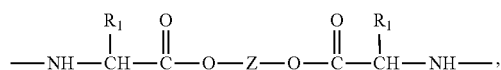

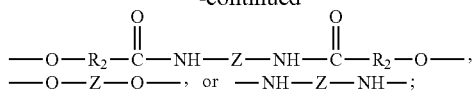

$M_1$ is a moiety represented by the structure

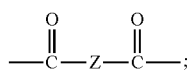

where $R_1$, $R_2$, $R_3$, X and Y are substituents and moieties as defined above;

Z is a moiety that can be derived from a compound selected from a group consisting of poly(ethylene glycol) (PEG), poly(propylene glycol) (PPG), random or block copolymers of PEG and PPG, hyaluronic acid, poly(2-hydroxyethyl methacrylate), poly(3-hydroxypropylmethacrylamide), poly(styrene sulfonate), poly(vinyl pyrrolidone), and cellulosics; and m, n, and p are independent integers where the value of m can be between 5 and 1,800, the value of n can be between 1 and 800 and the value of p can be between 4 and 1,500.

Some other exemplary methods of forming a PEA unit or moiety is described in U.S. application Ser. No. 10/805,036, published as US-2005-0208091-A1, the teachings of which are incorporated herein in their entirety by reference.

In some embodiments, the PEA polymer can include units derived from a diamine or a diol with one or more carboxylic acid substituent. Some examples of such PEA polymers, include, but are not limited to, the ones shown below (Table 7).

TABLE 7

Exemplary PEA polymers $[A]_n-[B]_m-[C]_o$ where [A] is

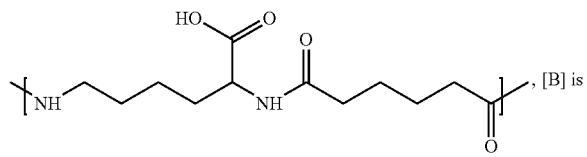

, [B] is

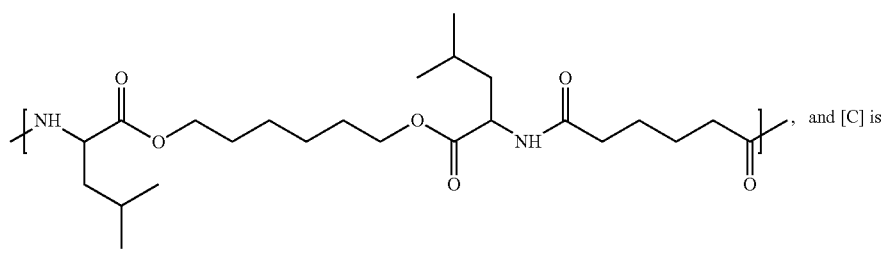

, and [C] is

TABLE 7-continued

Exemplary PEA polymers

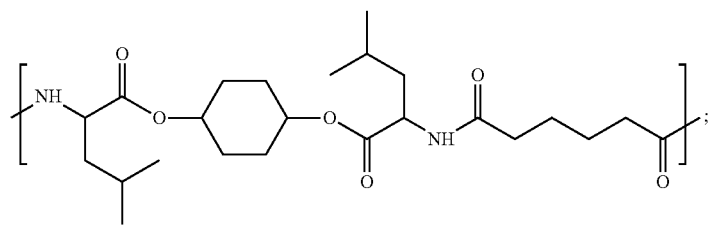

$[A]_m$-$[B]_n$ where [A] is

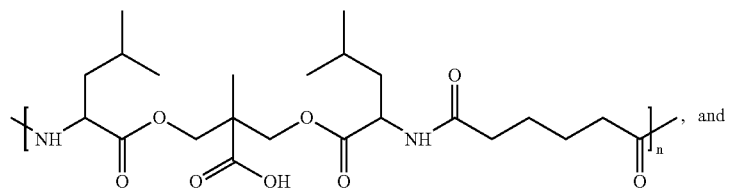, and

[B] is

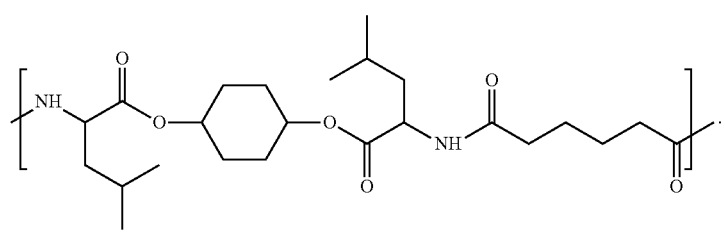.

In Table 7, m, n, and o are independent integers ranging from 1 to about 100,000, e.g., from about 5 to about 50,000, from about 10 to about 10,000, from about 100 to about 5,000, from about 500 to about 2,000 or about 1,000.

In some embodiments, a PEA polymer can include different diacids in the same PEA polymer.

In some embodiments, a PEA polymer described herein can include units derived from leucine, alanine, and/or phenyl alanine.

In some embodiments, a PEA polymer described herein can include units derived from adipate and/or sebacinate.

Methods of Generating Free Carboxylic Acid Pendant Groups

The free carboxylic acid group can be attached to or generated in a PEA polymer via any documented methodologies. For example, a compound including a protected free carboxylic acid can be attached to a PEA polymer via the functional groups on the PEA polymer backbone. Deprotection of the carboxylic acid group will generate the free carboxylic acid groups attached to the PEA polymer backbone. Attachment of such compound to the PEA polymer can be readily achieved by an ordinary artisan using established methodologies. Examples include modifying a free pendant alcohol to an acid group by reacting it with an cyclic anhydride such as succinic anhydride, or modifying ketones into carboxylic groups (see, e.g., J. F. Gohy, S. Antoun, R. Sobry, G. Van den Bossche, R. Jérôme, Macromol. Chem. Phys., 201, 31-41 (2000); Ph. Lecomte, D. Mecerreyes, J. L. Hedrick, R. Jérôme Macromolecules, 2000, 33, 14-18)).

In some embodiments, a compound including a protected free carboxylic acid can be grafted to a PEA polymer via the functional groups on the PEA polymer backbone. Methods of grafting such compound to the PEA polymer are well documented, which includes, e.g., Bryan Parrish, Rebecca B. Breitenkamp, and Todd Emrick, "PEG- and Peptide-Grafted Aliphatic Polyesters by Click Chemistry" in J. Am. Chem. Soc., 127(20):7404-7410 (2005)).

In some embodiments, PEA polymers with free carboxylic acid pendant groups can be generated by conversion of a carboxylate pendant groups into carboxylic acid pendant groups. For example, $[A]_n$-$[B]_m$-$[C]_o$ where [A] is

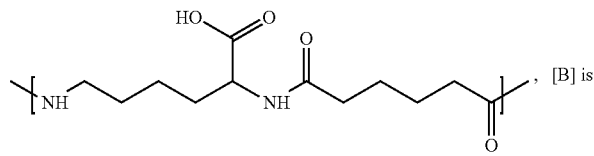, [B] is

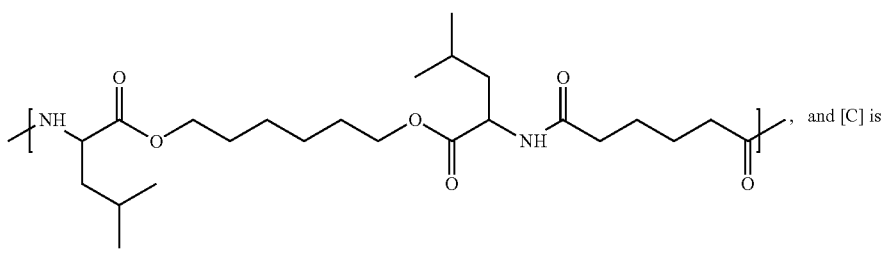, and [C] is

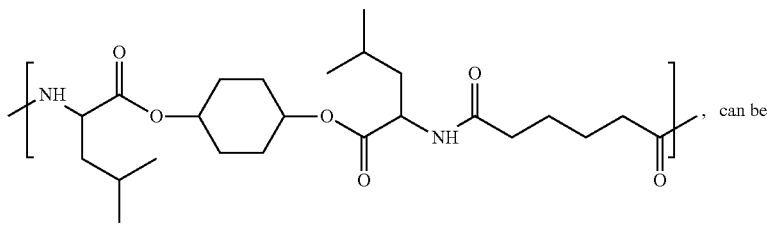, can be generated according to Scheme I (below) from $[A']_n\text{-}[B]_m\text{-}[C]_o$ where $[A']$ is

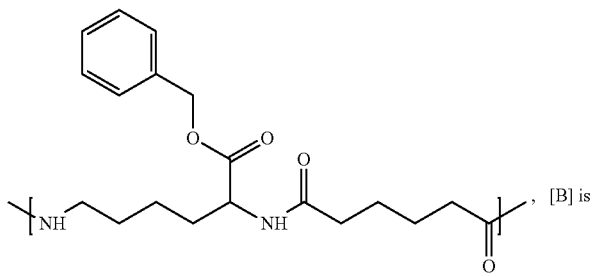, [B] is

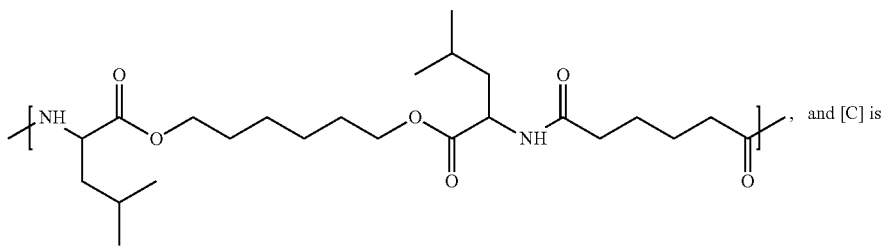, and [C] is

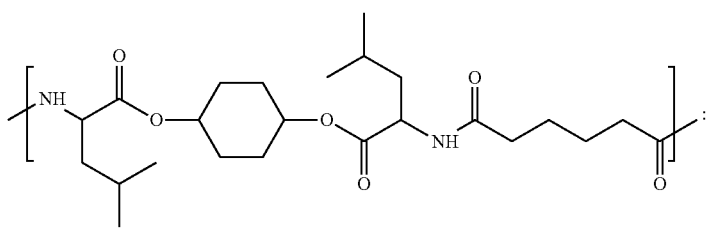;

Scheme I

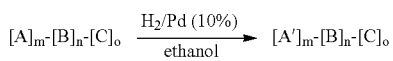

Figure 2:
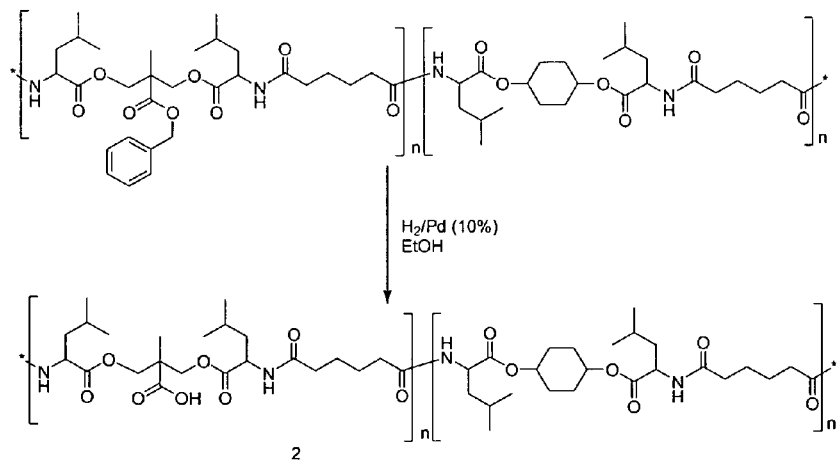

(see also Figures 1 and 2).

In some embodiments, benzyl ester protected bis-methylol propionic acid (bis-MPA) can be used as a spacer to couple two amino acids to generate a diamine. This diamine can be used to form a PEA with benzyl carboxylate pendant groups according to the general methodology described above.

Removal of the benzyl ester groups generate a PEA polymer with free carboxylic acid groups. One such polymer is $[A]_m\text{-}[B]_n$ where [A] is

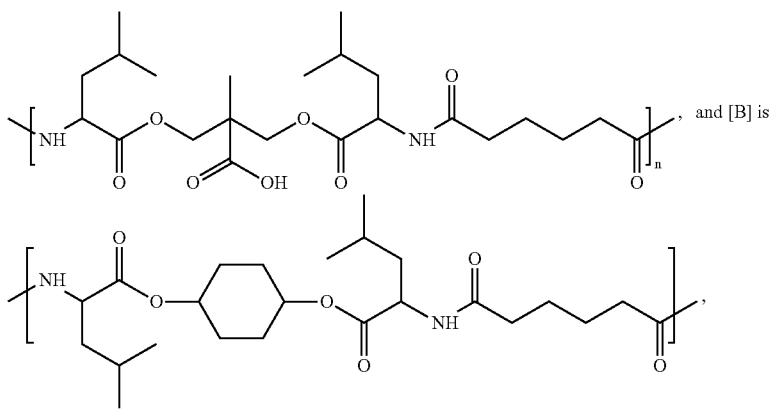, and [B] is which can be readily can be generated according to Scheme II (below) from $[A']_m\text{-}[B]_n$ where $[A']$ is

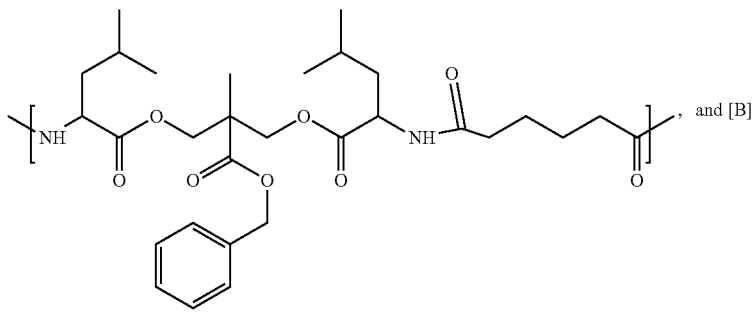

is

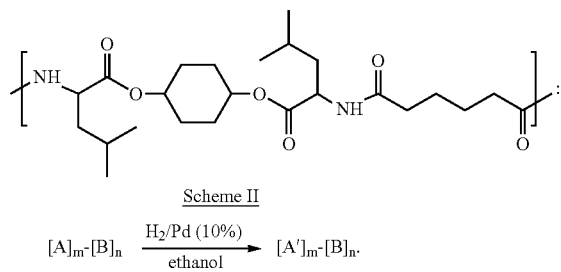

Scheme II $[A]_m\text{-}[B]_n \xrightarrow[\text{ethanol}]{\text{H}_2/\text{Pd (10\%)}} [A']_m\text{-}[B]_n.$ In Scheme I and II, m, n, o are independent integers as defined above.

Other Polymers

A coating can be formed of the PEA polymer described herein alone or with one or more other polymers. Representative polymers include, but are not limited to, poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanoate) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly(L-lactide-co-glycolide), polycaprolactone, poly(lactide-co-caprolactone), poly(glycolide-co-caprolactone), poly(dioxanone), poly(ortho esters), poly(trimethylene carbonate), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(iminocarbonate), polyurethanes, polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as HEMA, hydroxypropyl methacrylate (HPMA), hydroxypropylmethacrylamide, PEG acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly (tetramethylene glycol), hydroxy functional poly(vinyl pyrrolidone), biomolecules such as collagen, chitosan, alginate, fibrin, fibrinogen, cellulose, starch, collagen, dextran, dextrin, fragments and derivatives of hyaluronic acid, heparin, fragments and derivatives of heparin, glycosamino glycan (GAG), GAG derivatives, polysaccharide, elastin, chitosan, alginate, or combinations thereof. In some embodiments, the coating described herein can exclude any one of the aforementioned polymers.

In some embodiments, the coating can further include a biobeneficial material. The biobeneficial material can be polymeric or non-polymeric. The biobeneficial material is preferably substantially non-toxic, non-antigenic and non-immunogenic. A biobeneficial material is one that enhances the biocompatibility of a device by being non-fouling, hemocompatible, actively non-thrombogenic, or anti-inflammatory, all without depending on the release of a pharmaceutically active agent.

Representative biobeneficial materials include, but are not limited to, polyethers such as poly(ethylene glycol), copoly (ether-esters) (e.g. PEO/PLA), polyalkylene oxides such as poly(ethylene oxide), poly(propylene oxide), poly(ether ester), polyalkylene oxalates, polyphosphazenes, phosphoryl choline, choline, poly(aspirin), polymers and co-polymers of hydroxyl bearing monomers such as hydroxyethyl methacrylate (HEMA), hydroxypropyl methacrylate (HPMA), hydroxypropylmethacrylamide, poly (ethylene glycol) acrylate (PEGA), PEG methacrylate, 2-methacryloyloxyethylphosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as fibrin, fibrinogen, cellulose, starch, collagen, dextran, dextrin, hyaluronic acid, fragments and derivatives of hyaluronic acid, heparin, fragments and derivatives of heparin, glycosamino glycan (GAG), GAG derivatives, polysaccharide, elastin, chitosan, alginate, silicones, PolyActive™, or combinations thereof. In some embodiments, the coating can exclude any one of the aforementioned polymers.

The term PolyActive™ refers to a block copolymer having flexible poly(ethylene glycol) and poly(butylene terephthalate) blocks (PEGT/PBT). PolyActive™ is intended to include AB, ABA, BAB copolymers having such segments of PEG and PBT (e.g., poly(ethylene glycol)-block-poly(butyleneterephthalate)-block poly(ethylene glycol) (PEG-PBT-PEG).

In a preferred embodiment, the biobeneficial material can be a polyether such as poly (ethylene glycol) (PEG) or polyalkylene oxide.

Bioactive Agents

In some embodiments, a coating that includes a aliphatic thioester polymer described herein can optionally include one or more bioactive agents. These bioactive agents can be any agent which is a therapeutic, prophylactic, or diagnostic agent. These agents can have anti-proliferative or anti-inflammatory properties or can have other properties such as antineoplastic, antiplatelet, anti-coagulant, anti-fibrin, anti-thrombotic, antimitotic, antibiotic, antiallergic, or antioxidant properties. Moreover, these agents can be cystostatic agents, agents that promote the healing of the endothelium, or agents that promote the attachment, migration and proliferation of endothelial cells while quenching smooth muscle cell proliferation. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules, which bind to complementary DNA to inhibit transcription, and ribozymes. Some other examples of bioactive agents include antibodies, receptor ligands, enzymes, adhesion peptides, blood clotting factors, inhibitors or clot dissolving agents, such as streptokinase and tissue plasminogen activator, antigens for immunization, hormones and growth factors, oligonucleotides such as antisense oligonucleotides and ribozymes and retroviral vectors for use in gene therapy. Examples of anti-proliferative agents include rapamycin and its functional or structural derivatives, 40-O-(2-hydroxy)ethyl-rapamycin (everolimus), and its functional or structural derivatives, paclitaxel and its functional and structural derivatives. Examples of rapamycin derivatives include ABT-578, 40-O-(3-hydroxy)propyl-rapamycin, 40-O-[2-(2-hydroxy)ethoxy]ethyl-rapamycin, and 40-O-tetrazole-rapamycin. Examples of paclitaxel derivatives include docetaxel. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N. J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of anti-inflammatory agents including steroidal and non-steroidal anti-inflammatory agents include biolimus, tacrolimus, dexamethasone, clobetasol, corticosteroids or combinations thereof. Examples of such cytostatic substances include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, pimecrolimus, imatinib mesylate, midostaurin, and genetically engineered epithelial cells. The foregoing substances can also be used in the form of prodrugs or co-drugs thereof. The foregoing substances also include metabolites thereof and/or prodrugs of the metabolites. The foregoing substances are listed by way of example and are not meant to be limiting. Other active agents which are currently available or that may be developed in the future are equally applicable.

In some embodiments, a coating including an aliphatic thioester polymer described herein can specifically exclude any one or more of the above described agents.

The dosage or concentration of the bioactive agent required to produce a favorable therapeutic effect should be less than the level at which the bioactive agent produces toxic effects and greater than the level at which non-therapeutic results are obtained. The dosage or concentration of the bioactive agent can depend upon factors such as the particular circumstances of the patient, the nature of the trauma, the nature of the therapy desired, the time over which the ingredient administered resides at the vascular site, and if other active agents are employed, the nature and type of the substance or combination of substances. Therapeutically effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by those of ordinary skill in the art.

Examples of Medical Devices

As used herein, a medical device may be any suitable medical substrate that can be implanted in a human or veterinary patient. Examples of such medical devices include self-expandable stents, balloon-expandable stents, stent-grafts, grafts (e.g., aortic grafts), heart valve prostheses, cerebrospinal fluid shunts, pacemaker electrodes, catheters, and endocardial leads (e.g., FINELINE and ENDOTAK, available from Guidant Corporation, Santa Clara, Calif.), anastomotic devices and connectors, orthopedic implants such as screws, spinal implants, and electro-stimulatory devices. The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable (e.g., bioabsorbable stent) or biostable polymers could also be used with the embodiments of the present invention.

Method of Use

Preferably, the medical device is a stent. The stent described herein is useful for a variety of medical procedures, including, by way of example, treatment of obstructions caused by tumors in bile ducts, esophagus, trachea/bronchi and other biological passageways. A stent having the above-described coating is particularly useful for treating diseased regions of blood vessels caused by lipid deposition, monocyte or macrophage infiltration, or dysfunctional endothelium or a combination thereof, or occluded regions of blood vessels caused by abnormal or inappropriate migration and proliferation of smooth muscle cells, thrombosis, and restenosis. Stents may be placed in a wide array of blood vessels, both arteries and veins. Representative examples of sites include the iliac, renal, carotid and coronary arteries.

For implantation of a stent, an angiogram is first performed to determine the appropriate positioning for stent therapy. An angiogram is typically accomplished by injecting a radiopaque contrasting agent through a catheter inserted into an artery or vein as an x-ray is taken. A guidewire is then advanced through the lesion or proposed site of treatment. Over the guidewire is passed a delivery catheter that allows a stent in its collapsed configuration to be inserted into the passageway. The delivery catheter is inserted either percutaneously or by surgery into the femoral artery, radial artery, brachial artery, femoral vein, or brachial vein, and advanced into the appropriate blood vessel by steering the catheter through the vascular system under fluoroscopic guidance. A stent having the above-described coating may then be expanded at the desired area of treatment. A post-insertion angiogram may also be utilized to confirm appropriate positioning.

The implantable device can be implanted in any mammal, e.g., an animal or a human being. In some embodiments, the implantable device can be implanted in a patient in need of treatment by the implantable device. The treatment can be angioplasty or other type of treatments involving an implantable device. A patient who receives the implantable device described herein can be male or female under normal body condition (e.g., normal weight) or abnormal body condition (e.g., underweight or overweight). The patient can be in any age, preferably, the patient is in an age ranging from about 40 to 70 years. An index for measuring the body condition of a patient is BMI (body mass index). A patient can have a BMI ranging from about 18 to about 30 or above.

The implantable device described herein can be used to treat or ameliorate a medical condition such as atherosclerosis, thrombosis, restenosis, hemorrhage, vascular dissection or perforation, vascular aneurysm, vulnerable plaque, chronic total occlusion, claudication, type-II diabetes, anastomotic proliferation for vein and artificial grafts, bile duct obstruction, ureter obstruction, tumor obstruction, or combinations thereof.

EXAMPLES

The embodiments of the present invention will be illustrated by the following prophetic examples. All parameters and data are not to be construed to unduly limit the scope of the embodiments of the invention.

Example 1. Synthesis of New PEA Polymers

A typical example of the new PEA (1) as designed for a drug-delivery coating described herein is shown in FIG. 1, which shows the deprotection step in its synthetic route, where the free acid is generated from a benzyl ester protected lysine. The acid containing monomer can be incorporated at any amount.

An alternative design is through the use of benzyl ester protected bis-methylol propionic acid (bis-MPA) as a spacer between two amino acids, which are subsequently deprotected to generate the desired type of polymers 2 (FIG. 2).

In FIGS. 1 and 2, the n numbers are independent integers and can be 1 to about 100,000, e.g., from about 5 to about 50,000, from about 10 to about 10,000, from about 100 to about 5,000, from about 500 to about 2,000 or about 1,000.

The above mentioned polymers could be made with any spacer lengths (diols, diacids) as well as from any type of amino acids. Alternatively, the polymers could also comprise oligoethyleneoxide linkages to increase their hydrophilicity which would help to promote swelling and acid catalyzed degradation.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical device comprising a coating, the coating comprising a poly(ester amide) (PEA) polymer comprising free carboxylic acid pendant groups, wherein the free carboxylic acid pendant groups are from 2,2-dimethylolpropionic acid, wherein the PEA polymer is of formula:

[A]$_m$-[B]$_n$;

wherein:

[A] is

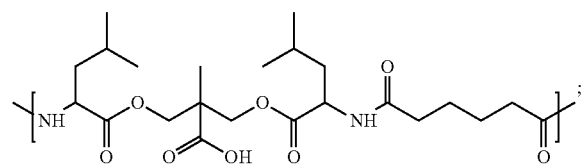

[B] is

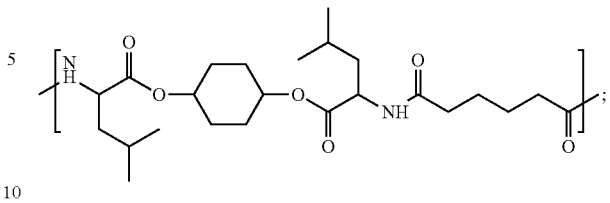

m and n are independently integers ranging from 1 to about 100,000.

2. The medical device of claim 1, wherein the PEA polymer has an acid content of about 0.01% or above.

3. The medical device of claim 1, wherein the PEA polymer has an acid content of about 0.1% or above.

4. The medical device of claim 1, wherein the PEA polymer has an acid content of about 1% or above.

5. The medical device of claim 1, wherein the PEA polymer has an acid content of about 5% or above.

6. The medical device of claim 1, wherein the PEA polymer has an acid content of about 10% or above.

7. The medical device of claim 1, further comprising a bioactive agent.

8. The medical device of claim 7, wherein the bioactive agent is paclitaxel, docetaxel, estradiol, 17-beta-estradiol, nitric oxide donors, super oxide dismutase, 4-amino-2,2,6, 6-tetramethylpiperidine-1-oxyl (4-amino-TEMPO), tacrolimus, dexamethasone, dexamethasone acetate, rapamycin, 40-O-(2-hydroxy)ethyl-rapamycin (everolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (ABT-578), γ-hiridun, clobetasol, mometasone, pimecrolimus, imatinib mesylate, or midostaurin.

9. The medical device of claim 8, wherein the bioactive agent is everolimus.

10. The medical device of claim 1 which is a stent.

11. The medical device of claim 1 which is a bioabsorbable stent.

12. A method of treating or ameliorating a medical condition, comprising implanting in a human being the medical device of claim 7, wherein the medical condition is selected from atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

13. A method of treating or ameliorating a medical condition, comprising implanting in a human being the medical device of claim 8, wherein the medical condition is selected from atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, urethra obstruction, tumor obstruction, diabetic vascular disease, and combinations thereof.

* * * * *